US008642551B2

(12) United States Patent
Diaz Gil

(10) Patent No.: US 8,642,551 B2
(45) Date of Patent: Feb. 4, 2014

(54) USE OF LIVER GROWTH FACTOR (LGF) AS A NEURAL TISSUE REGENERATOR

(75) Inventor: Juan Jose Diaz Gil, Madrid (ES)

(73) Assignee: Juan José Díaz Gil, Madrid (ES)

( * ) Notice: Subject to any disclaimer, the term of this patent is extended or adjusted under 35 U.S.C. 154(b) by 510 days.

(21) Appl. No.: 12/988,448

(22) PCT Filed: Apr. 17, 2009

(86) PCT No.: PCT/ES2009/070106
§ 371 (c)(1),
(2), (4) Date: Oct. 18, 2010

(87) PCT Pub. No.: WO2009/127768
PCT Pub. Date: Oct. 22, 2009

(65) Prior Publication Data
US 2011/0034382 A1   Feb. 10, 2011

(30) Foreign Application Priority Data

Apr. 18, 2008 (ES) .................................. 200801121

(51) Int. Cl.
*A61K 35/407* (2006.01)
*A61K 38/18* (2006.01)
*A61K 38/38* (2006.01)
*C07K 14/475* (2006.01)

(52) U.S. Cl.
USPC ......... 514/17.7; 514/15.2; 514/776; 530/399; 530/830

(58) Field of Classification Search
None
See application file for complete search history.

(56) References Cited

FOREIGN PATENT DOCUMENTS

WO    2007 122280    11/2007

OTHER PUBLICATIONS

Bibliographic data sheet for WO2007/122280, showing that WO2007/122280 was also published as ES2325699; Nov. 1, 2007.*
Machine translation of ES2325699 (Diaz); Sep. 14, 2009; 21 pages total.*
Gonzalo-Gobernado et al., J Histochem Cytochem 2009 57: 491-502.*
Shao and Diamond, Human Molecular Genetics, 2007, 16: R115-R123.*
Morren and Galvez-Jimenez, Expert Opin Investig Drugs, 2012; 21: 297-320.*
Desai et al., Cell Tranplantation, 2007; 285-299.*
Bartels et al., Current Pharmaceutical Design, 2011; 17: 2771-2777.*
Diaz-Gil et al., Biochem J., 1986; 235: 49-55.*
Bazan, E. et al., "LGF (Liver Growth Factor) como factor de proliferacion, migracion y diferenciacion de las celulas madre neurales y su possible utilidad en enfermedad de Parkinson LGF (Liver Growth Factor) as a factor involved in the proliferation, migration and differentiation of neural stem cells: Potential use in Parkinson's disease", Mapfre Medicina, vol. 16, No. 4, pp. 237-247, (2005).
Reimers, Diana et al., "Intrastriatal Infusion of Liver Growth Factor Stimulates Dopamine Terminal Sprouting and Partially Restores Motor Function in 6-Hydroxydopamine-lesioned Rats", Journal of Histochemical & Cytochemistry, vol. 54, No. 4, pp. 457-465, (2006).
Gonzalo-Gobernado, R. et al., "Liver Growth Factor Stimulates Proliferation and Migration of Adult Neural Stem Cells of Subventricuar Zone in Parkinsonian Rats," Rev., Neurol., vol. 45, pp. 187, (2007), (with English translation).
International Search Report issued Aug. 6, 2009 in PCT/ES09/070106 filed Apr. 17, 2009.
Aron, L. and Klein, R. Repairing the Parkinsonian Brain with Neurotrophic Factors. Trends Neuroscience, Elsevier Ltd. Feb. 2011, 34(2): 88-100.
Patel, NK and Gill, SS. GDNF Delivery for Parkinson's Disease. Acta Neurochir Suppl. 2007, 97(Pt 2): 135-154.
Skaper, SD. Peptide Mimetics of Neurotrophins and their Receptors. Curr Pharm Des. 2011, 17(25):2704-18.
Pardridge, William M. The Blood-Brain Barrier:Bottleneck in Brain Drug Development. The Journal of the American Society. NeuroRx. 2005, vol. 2, No. 1., p. 3-14.
Gonzalo-Gobernado, Rafael, et al. Neuroprotective Activity of Peripherally Adminstered Liver Growth Factor in a Rat Model of Parkinson's Disease. PLoS One 8(7):e67771. Jul. 2013.
Reimers, Diana, et al. Liver Growth Factor Promotes the Survival of Grafted Neural Stem Cells in a Rat model of Parkinson's Disease. Current Stem Cell Research & Therapy. Bentham Science Publishers. 2012. vol. 7, No. 1, pp. 15-25.

* cited by examiner

*Primary Examiner* — Bridget E Bunner
*Assistant Examiner* — Christina Borgeest
(74) *Attorney, Agent, or Firm* — Oblon, Spivak, McClelland, Maier & Neustadt, L.L.P.

(57) ABSTRACT

The invention comprises the use of LGF in the production of medicinal products that can be used in the pleiotropic tissue regeneration of one or more damaged tissues, in which at least one of the damaged tissues forms part of the central nervous system and the medicinal product is intended to be administered systemically. The invention is based on the fact that intraperitoneal administration of LGF can promote a positive effect on a Parkinson's disease model. As such, in a preferred embodiment of the invention, the medicinal product is intended for the treatment of Parkinson's disease, particularly when the medicinal product is intended for humans.

5 Claims, 1 Drawing Sheet

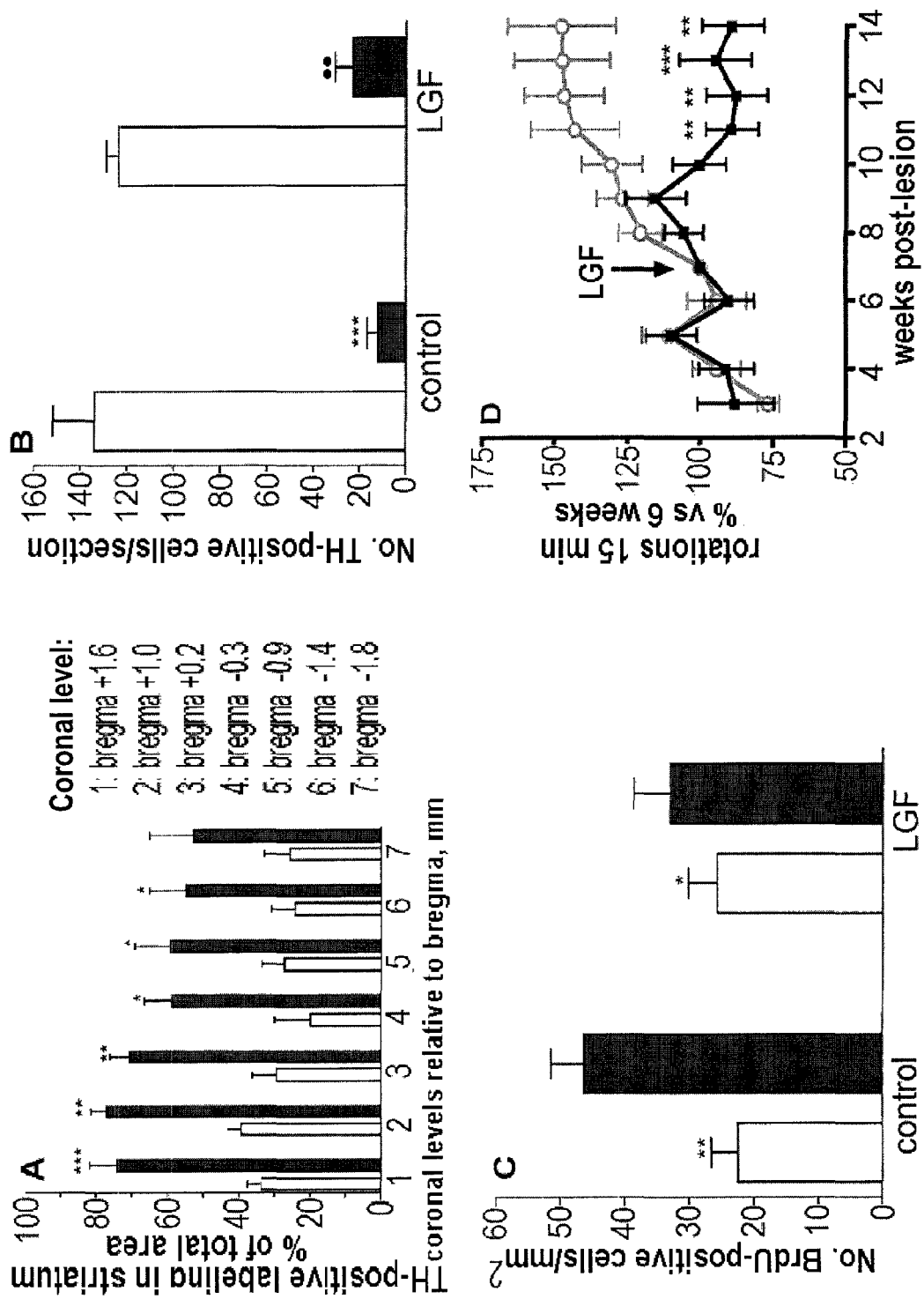

USE OF LIVER GROWTH FACTOR (LGF) AS A NEURAL TISSUE REGENERATOR

This application is a National Stage of PCT/ES09/070,106 filed Apr. 17, 2009 and claims the benefit of Spanish application 200801121 filed Apr. 18, 2013.

FIELD OF TECHNOLOGY

The invention relates to the contribution of the use of liver growth factor (LGF) for the manufacture of a medicinal product for systemic administration in mammals for the treatment of a neurodegenerative disease, treatment of which requires tissue regeneration. Said invention represents an improvement of the invention presented in patent application ES200601018 and in international patent application PCT/ES2007/070080, in which the priority of the foregoing was claimed.

PRIOR ART

Liver growth factor (LGF), which was discovered some years ago (Díaz Gil et al., 1986), is a molecule purified from rat serum after 70% partial hepatectomy, or in rats with ligation of the biliary duct which, when injected in rats or mice, has activity "in vivo" as a growth factor, increasing the synthesis of liver DNA, the dry weight of the liver, the number of "PCNA-positive" cells (PCNA: proliferating cell nuclear antigen), producing transient hyperplasia with neither immediate nor permanent aggressive effects being detected: without production of fibrosis, amyloids, or mitochondrial or nuclear disorders (Díaz Gil et al., 1994).

Its chemical structure was defined by the same authors as an albumin-bilirubin complex, after investigation of absorption spectra, fluorescence, circular dichroism, tryptic maps, amino acid composition, electrophoretic mobility, immunofluorescence, formation of albumin-bilirubin complexes "in vitro", investigation of biological activity both "in vivo" and "in vitro" and identification by HPLC (Díaz Gil et al., 1987; Díaz Gil et al., 1988).

LGF also has activity "in vitro", in a primary culture of rat hepatocytes, increasing the synthesis of DNA, the cell count, the activity of the membrane transport system A and others (Díaz Gil et al., 1986). LGF has also been purified from serum of humans with type B hepatitis, with structure and characteristics almost identical to that from rats (Díaz Gil et al., 1989). Other authors (Abakumova et al., 1994) have confirmed the activity of albumin-bilirubin complexes as liver growth factors.

Furthermore, it has been demonstrated that LGF is able to stimulate the regeneration of the liver damaged by the action of various hepatotoxins (Díaz Gil et al., 1994b; Díaz Gil et al., 1999). In a model of cirrhosis induced by $CCl_4$, once an irreversible situation had been reached, injection of LGF was able to reduce fibrosis, producing a substantial remodelling of the hepatic parenchyma, improvement of inflammation and necrosis, increase in hepatic function and restoration of various haemodynamic functions, such as: portal pressure, arterial pressure, portosystemic shunting and systemic vascular resistance, as well as reduction of ascites. However, the extremely complex network that gives rise to the establishment of fibrosis in the various types of organs, although having various traits in common, has particular features depending on the organ in question, such that the antifibrotic action of LGF in the liver was not guaranteed to display the same ability in some other different organ.

In addition, and in research conducted by various groups principally on endothelial cells, three types of albumin receptors have been identified on the cell membrane, the three glycoproteins: gp60, with the main function of transcytosis, which principally passes albumin from one side to the other in endothelial cells (Ghinea et al., 1988), and two with the function of endocytosis, for taking up albumin into the cell, gp18 and gp31. These last-mentioned receptors bind preferentially to albumins in which their conformation has been modified for "binding" to a ligand. The affinity is 1000 times compared to what is observed with native albumin (Schnitzer et al., 1992). gp18 and gp31 are expressed preferentially in endothelial cells of fetal tissues, neonates or adults, higher concentrations being recorded in organs with very active proliferation or in phases of increased growth, in brain, lung, thymus, heart, skeletal muscle, liver, spinal cord, spleen, pancreas, testes, adenohypophysis, placenta, endometrium, myometrium and leukocytes (Morioanu et al., 1990).

The hypothesis used by these authors to explain the reasons for the universality and abundance of these receptors gp18 and gp31 in organs of almost every type is that they either serve: 1) to metabolize "modified albumins" (albumin with some other compounds bound to it, such as maleic anhydride, formaldehyde etc., which alters its conformation), which are known to exist in human serum at varying concentrations, or 2) to transport nutrients necessary for growth of cells of almost every type.

Taking into account the abundance of the receptors gp18 and gp31 in various tissues, their high concentration in organs with very active proliferation and the fact that the natural ligands of gp18 and gp31 are "modified albumins" (albumins with a conformational change, the same as happens with LGF, which is an albumin with a specific conformational change, connected with appearance of biological activity (see Díaz Gil et al., 1987)), the inventors thought that perhaps LGF might be able to act as a growth and regeneration factor in a great variety of tissues, just as they had demonstrated previously in the liver; finally, they decided to test the hypothesis of the validity of LGF as a tissue regeneration factor of the pleiotropic type, which was novel with respect to other strategies for use of LGF proposed so far. For example, the patent "Method for diagnosis and monitoring of hepatopathies by determination of liver growth factor in blood plasma and/or serum", publication number 2005259, was granted in 1989, but LGF was not contemplated as a possible therapeutic agent in the corresponding application.

The inventors demonstrated recently that the mitogenic action of LGF on the liver is mediated, at least partly, by TNF-α (Díaz Gil et al., 2003). They took this as an indication that LGF could also have mitogenic action on other tissues in which said cytokine can be expressed. However, the increase in TNF-α does not in itself produce mitogenic effects; in fact, it is closely linked to the acute phase, regardless of its aetiology: ischaemia, trauma, inflammation, toxicity (as reviewed by Ding W X et al., 2004, and Trauner M et al., 1999) and even when injected in rats it can give rise to endocrine and haematologic disorders (Kettelhut I et al., 1987); moreover, it is closely connected with cell death, both by necrosis and by apoptosis (reviewed by Malhi H et al., 2006). Since stimulation of TNF-α is associated both with effects of mitogenic stimulation and with effects of cell death, an increase in its expression induced by LGF does not describe the activity of LGF unambiguously. Moreover, LGF is able to induce mitosis in a culture of hepatocytes (Díaz Gil et al., 1986), in which there are no endothelial cells that could produce TNF-α. Accordingly, its possible use for inducing proliferation of tissues other than hepatic tissue and the effect that it might have on them remained to be demonstrated.

Following the line of the possible validity of LGF as a tissue regeneration factor, the inventors recently demonstrated the capacity of LGF for reducing hypertension in hypertensive rats by producing a decrease in fibrosis in the carotid artery and increasing the cell count of the vascular smooth musculature but without altering the inside diameter or the average thickness of said arteries (Somoza et al., 2006).

They also demonstrated the capacity of LGF for increasing the number of dopaminergic terminals in animal models of Parkinson's disease (Reimers D. et al., 2006). It was observed that LGF produces a notable increase in dopaminergic terminals, as well as an improvement in behaviour (rotational test). These results opened up a promising route regarding the possibility of using LGF in other fields of considerable interest. However, the experiments presented in this publication were conducted by administering LGF to mice by the intrastriatal route, i.e. administering it directly into the brain, without the need for it to cross the blood-brain barrier. Unfortunately this route of administration is not really feasible in human beings, so it is difficult to use it in actual clinical practice for the treatment of Parkinson's disease in human beings.

The capacity of LGF, following intraventricular application, for promoting the generation of new neurons and migration thereof into the denervated striatum was also demonstrated recently (Gonzalo-Gobernado et al., 2007).

This same line of research was reinforced by the findings described in patent application ES200601018. This describes the use of liver growth factor in the manufacture of a medicinal product used for pleiotropic tissue regeneration, based on the mitogenic effect in general and the angiogenesis stimulating effect in particular that LGF exerts on various organs, such as the testes, the spinal cord or the skin, as well as its antifibrotic activity in coronary arteries, its capacity for remodelling the walls of coronary arteries and arteries of the greater and lesser circulation, its ability to stimulate anticholesterolaemic enzymes such as paraoxonase-1 and the inhibitory effect on the growth of liver carcinoma cells. These effects of LGF mean it can be used for the treatment of pathologies such as atherosclerosis, coronary disease, thrombosis or liver carcinoma, as well as helping in the recovery of damaged tissues such as those of the testes, spinal cord, infarcted heart, fractured bone, damaged skin or any other tissue whose recovery is accelerated by stimulation of angiogenesis.

The method of administration of LGF in the experiments relating to regeneration of the spinal cord was intraperitoneal injection of LGF. Two different situations were included: in the first of these, traumatic lesion was produced and fetal cells were transplanted two months later, LGF being injected immediately, 4 injections in 2 weeks. In the second situation, trauma or hemisection of the spinal cord was produced, LGF being injected one week later (4 injections in 2 weeks). Now, owing to the characteristics of the models used, the blood-brain barrier (BSCB, blood spinal cord barrier) was profoundly altered as a consequence of the aggressive action to which it was submitted. This circumstance has been extensively investigated by various authors: thus, the immediate damage produced in the BSCB after mechanical trauma is known (Maikos and Shreiber, 2007). To quantify this permeability, researchers have used compounds of low molecular weight, $^{14}C$-α-aminoisobutyric, increased permeability being detected 28 days after the trauma (Popovich et al., 1996), and compounds of higher molecular weight: for example by infusion of $^{14}C$-albumin (Wood et al., 1999; Pettersson et al., 1990; Sharma, 2004), by injection of horseradish peroxidase, HRP (Jaeger et al., 1997), using luciferase (Whetstone et al., 2003), or techniques of magnetic resonance, MRI (Bilgen et al., 2001; Bilgen et al., 2002). In addition, loss of albumin at the site of the lesion was detected by immunohistochemical methods (Gordh et al., 2006), even ten weeks after the trauma, a longer period than was used in the experiments in patent applications ES200801121 and PCT/ES2007/070080. It can be concluded from the foregoing that the increase in permeability of the BSCB as a result of trauma has been demonstrated by many authors, and is known by a person skilled in the art, and occurs in both directions, from the medulla to the outside and vice versa, and that it is maintained for a longer time than that including injection of LGF in the second situation described above. Additionally, in the first situation, LGF was injected two months after the trauma, before transplant of fetal cells, but precisely this fact also alters the permeability of the BSCB (Horner et al., 1996), this increased permeability having been detected up to two weeks after the transplant.

Based on the foregoing, a person skilled in the art would consider that the positive effects of LGF observed in spinal cord regeneration would be attributable to the increase in permeability of the blood-brain barrier that is produced because the latter is altered, which makes it possible for LGF to bind to the medulla without it being necessary that the intact blood-brain barrier is permeable to it.

Moreover, growth factors, in general, are not compounds that can easily cross the blood-brain barrier. Except in the case of IGF (insulin-like growth factor) (Reinhardt and Bondy, 1994) it is generally considered that the other growth factors do not cross this barrier. Although the ability to cross the blood-brain barrier does not depend exclusively on size, since LGF has a considerable molecular weight, 64 000 kDa, this means a priori that it is unlikely that it crosses the blood-brain barrier.

Thus, the search for therapeutic agents that can be used for regeneration of damaged tissues belonging to the central nervous system and accordingly the prevention and/or treatment of disorders or diseases in which said tissues are involved, such as Parkinson's disease, is made difficult, in general, by the problem of finding a compound that has the required therapeutic activity and, at the same time, is able to cross the blood-brain barrier, thus making possible its administration by routes that can be applied in human beings, such as those providing systemic administration (intravenous, intraperitoneal, intramuscular etc.).

The present patent application offers a solution to this problem.

BRIEF DESCRIPTION OF THE INVENTION

The present invention offers a solution to the problem of the manufacture of medicinal products designed to be administered systemically, directed at the treatment of neurodegenerative diseases that require the regeneration of damaged nerve tissue, it being demonstrated that LGF, administered systemically, is able to produce effects in tissues of the central nervous system, which are, therefore, on the other side of the blood-brain barrier. Thus, the invention of the present application offers an improvement of the invention disclosed in application ES200601018, demonstrating the specific usability of LGF for the regeneration of nerve tissue belonging to the central nervous system even when LGF is administered by a route that means that the desired effect must be produced on the other side of the blood-brain barrier.

The fact that LGF, administered systemically, is able to exert an effect on the other side of the blood-brain barrier, permits the treatment of neurodegenerative diseases that afflict mammals in which the blood-brain barrier is intact or minimally altered, without the need to supply the medicinal product by a route that requires direct administration to the central nervous system, such as the intracranial route: intrastriatal, intrathecal or intraventricular.

Thus, one object of the present invention is the use of liver growth factor (LGF) in the manufacture of medicinal products for use in tissue regeneration of one or more damaged tissues, characterized in that at least one of the tissues forms part of the central nervous system (CNS) and the medicinal product is designed to be administered systemically.

In a preferred embodiment of the invention, the medicinal product is designed for the treatment of a neurodegenerative disease. It is particularly preferable for the medicinal product to be designed for the treatment of Parkinson's disease, although other embodiments of the invention are also possible in which the disease is selected from other neurodegenerative diseases, such as Huntington's disease, ataxia and amyotrophic lateral sclerosis. Whatever the disease, it is preferred very especially that the individual for which the medicinal product is designed is a human being.

In another preferred embodiment of the invention, the medicinal product is designed to be administered by the intravenous or intraperitoneal route.

The invention also relates to a method of treatment of a disorder or disease whose severity or risk of deterioration decrease with the regeneration of one or more tissues, in which said disorder or disease is selected from those associated with the central nervous system, said method comprising the administration of liver growth factor by the systemic route to a human being or an animal. In a preferred embodiment of the method of the invention, LGF is administered by the intraperitoneal route. In another preferred embodiment of the method of the invention, LGF is administered by the intravenous route.

BRIEF DESCRIPTION OF THE DRAWINGS

FIGS. 1A-1D show the effects of intraperitoneal injection of LGF in rats with striatal lesion with 6-OHDA.

A shows, in various coronal sections, the percentage of the total area of the striatum with TH-positive innervation in control animals (white bar) and in animals treated with LGF (black bar). The distance, in millimetres, from bregma to each of the seven levels of the striatum in which the coronal sections were made, is shown on the right of the diagram.

B shows the effect of saline (control) and LGF i.p. on the number of dopaminergic neurons of the healthy (white bars) and damaged (black bars) *substantia nigra*.

C shows the effect of the administration i.p of saline (control) or LGF on the incorporation of BrdU in the healthy (white bars) and damaged (black bars) striatum.

D shows the rotational behaviour, evaluated by the apomorphine test, of the control animals (empty circles) and those injected i.p. with LGF (black squares).

The results represent the mean value±SEM of 5 (B and C), 10 (A) or 15 (D) independent animals. In A and B, $*p \leq 0.05$, $p \leq 0.01$, $*p \leq 0.001$ vs control animals. In B $***p \leq 0.001$ vs healthy control side, $\bullet\bullet p \leq 0.01$ vs healthy LGF side. In C $*\leq p0.05$, $**\leq p0.01$ vs damaged control side.

DETAILED DESCRIPTION OF THE INVENTION

As already mentioned, the closest precedent of the action of LGF on the brain is a publication describing the action of LGF, administered by intrastriatal infusion, on rats with Parkinson's disease (Reimer et al., 2006). The present invention relates to the data of LGF in the same model of Parkinson's, this time administering the LGF by the intraperitoneal route (LGF has the same biological activity by the intravenous route). The difference in the route of administration of LGF and its activity in the brain is a key point in the invention described in the present patent application and is closely associated with the concept of blood-brain barrier (hereinafter blood-brain barrier).

The blood-brain barrier was discovered in 1885 by Paul Ehrlich, who by intravenous injection of the dye trypan blue in rabbits, observed that all the organs were stained equally, apart from the brain. Eighty years later, it was discovered that the blood-brain barrier is constituted of the endothelial cells of the capillaries of the brain, which have very well sealed connections and constitute a very effective physical barrier (Reese et al., 1967). Penetration through the blood-brain barrier is not a question of molecular size alone, since 98% of small molecules, with molecular weight below 400, do not cross the blood-brain barrier. Furthermore, larger biotechnology products, such as monoclonal antibodies, recombinant proteins, compounds of "antisense" RNA or gene products do not cross the blood-brain barrier (see Pardridge, 2005 for a review). Similarly, a priori it seems unlikely that LGF, which is a large molecule, can cross the blood-brain barrier.

Despite the large number of patients with CNS disorders and the small number of molecules that cross the blood-brain barrier, fewer than 1% of pharmaceutical companies have specific programmes for researching products for solving this problem. The few components of low molecular weight for use in the brain have mainly focused on the treatment of depression, schizophrenia, chronic pain and epilepsy, and in the case of Parkinson's disease, only the administration of L-DOPA, a precursor of dopamine (Lloyd et al., 1970) has been used. In an attempt to solve this problem, several strategies have been devised based on transport mediated by receptors, monoclonal antibodies used as "Trojan horses", masking molecules with therapeutic action, such as recombinant proteins, antibodies, interference RNA and some others (see Pardridge, 2007, for a recent review).

The known activity of other growth factors that have demonstrated activity when infused intracranially in experimental models of Parkinson's is closely related with this point: transforming growth factor of the alpha type, TGF-α (Fallon et al., 2000), vascular endothelial growth factor, VEGF (Sun et al., 2003), glial cell line-derived neurotrophic factor, GDNF, or the combination of this and brain-derived neurotrophic factor, BDNF (Torp et al., 2006). In all cases, although cerebral activity has been demonstrated by intracranial infusion, it has not been demonstrated that they act by the intravenous or intraperitoneal route, possibly because they do not cross the blood-brain barrier.

Based on the foregoing, it would be expected that the action of LGF on the brain by the intracranial route will not ensure that said LGF has a biological effect by the intravenous or intraperitoneal route when the blood-brain barrier is intact.

However, research subsequent to submission of patent application ES200601018 demonstrated a surprising effect of the action of LGF, administered intraperitoneally, in the treatment of Parkinson's disease in mammals with an intact blood-brain barrier, as is presented later in the examples of the present specification, which give the results of injection of LGF by the intraperitoneal route.

Since the experiments relating to the administration of LGF for regeneration of the spinal cord, described in patent application ES200601018, show that LGF is capable of regenerating the tissue of the damaged spinal cord, it can be considered that LGF has the ability to regenerate, in general, nerve tissue of the central nervous system. Therefore its use can be extended to the manufacture of medicinal products for the treatment of any neurodegenerative disease that requires the regeneration of nerve tissue, in which the medicinal product is designed to be administered systemically, giving rise to an improvement of the pathologic situations described and a stimulating effect on regenerative processes in various tissues.

In addition, it is shown in Example 2 of the present patent application that LGF, injected by the intraperitoneal route, is able to stimulate the serotonin pathway in the brain in intact rats. Serotonin is a neurotransmitter with very varied functions, with decisive action and influence in many situations. Thus, it is known to participate in brain development (Azmitia et al., 2007), in memory (Buhot et al., 2000), in Alzheimer's disease (Meltzer et al., 1998), in epilepsy (Bagdy et al., 2007), in sleep (Gao et al., 2002), in dementia (Yan et al., 2001), in depression (Grahame-Smith et al., 1992), in anorexia and bulimia (Kaye et al., 2005), and in many others (see Smythies et al., 2005 for a review).

Activation of the serotonin pathway promoted by LGF administered by the intraperitoneal route lends more support to the usefulness of LGF for neurodegenerative diseases other than Parkinson's disease, such as Huntington's disease, amyotrophic lateral sclerosis, ataxias, etc.

The fact that LGF is able to exert an effect on the central nervous system when administered systemically implies that, regardless of the specific route of administration employed, whenever it has the result that LGF reaches the blood system and can reach the blood-brain barrier by the systemic route, the medicinal product will be able to produce a therapeutic effect on the desired neurodegenerative disease. Therefore there are possible embodiments of the invention in which the medicinal product is designed to be administered by the intraperitoneal route, as in the examples of the invention, but also those in which the medicinal product is designed to be administered by the intravenous route.

Regarding the composition of the medicinal product, those are preferred that include a pharmaceutically acceptable aqueous vehicle, in which the LGF is dissolved. Particularly saline medium, and very particularly hypotonic saline medium, are preferred. In addition, the medicinal product can contain any pharmaceutically suitable excipient, such as, for example, one or more stabilizers. Another especially preferred possibility is that in which the medicinal product includes LGF in lyophilized form, in a vacuum-sealed container, with optional additional presence of the saline vehicle in the same medicinal product; this presentation makes it possible to prepare the LGF solution shortly before it is administered.

The present invention will now be explained in more detail on the basis of the Examples and Drawings that are presented below, which are certainly not intended to limit the scope of the invention.

EXAMPLES

Example 1

Effects of Intraperitoneal Administration of LGF on Induction of Axonal Growth and Neurogenesis Since the results given in the article of Reimers et al. provide a basis for the possible use of LGF in the treatment of Parkinson's disease, the present experiment was conducted to test whether, on administering LGF by a route that will mean that the effects tested must be evaluated on the other side of the blood-brain barrier, positive effects were also observed in a model of said disease.

Thus, to verify the possibility that LGF can be used as a therapeutic tool administered by a route whose use is feasible in human beings, the effects of intraperitoneal administration of LGF on the induction of axonal growth and neurogenesis were investigated in the experimental model of Parkinson's disease described by Kirik et al. (1998).

The experimental model of Parkinson's disease used comprises the unilateral application of 4 injections of 6-hydroxydopamine (6-OHDA) at various points of the right striatum of female Sprague-Dawley rats weighing 200-220 g. For this, a 10 µl Hamilton microsyringe was used, at an injection rate of 1 µl/min. After application of the neurotoxin, the cannula was left in place for a further 2 min before being withdrawn slowly. The dose and coordinates used were selected on the basis of other works (Kirik et al., 1998). Concretely, the 6-OHDA was administered at a concentration of 3.5 µg/µl, 2 µl per injection (7 µg of 6-OHDA per injection). The stereotaxic coordinates (AP: anteroposterior; L: lateral; V: ventral) relative to the bregma (point on the surface of the skull at the junction of the coronal and digital sutures) and the dura, of each injection, were as follows:

1: AP: +1.3 mm; L: +2.6 mm; V: −5.0 mm
2: AP: +0.4 mm; L: +3.0 mm; V: −5.0 mm
3: AP: −0.4 mm; L: +4.2 mm; V: −5.0 mm
4: AP: −1.3 mm; L: +4.5 mm; V: −5.0 mm

In all cases, the incision bar was adjusted to 0 mm.

To determine the degree of lesion, a rotational behaviour test was performed at 15 days (subcutaneous injection of apomorphine 0.05 mg/kg). Injection of apomorphine induces rotational behaviour contralateral to the lesion. Animals that rotated 100 or more times in 15 minutes were considered to have lesions, and those that did not meet this criterion were discarded. During the period prior to treatment with LGF, regular weekly rotation tests were conducted, in order to ensure complete establishment of the lesion.

Eight weeks after the lesion, the animals were divided into two groups: treated with LGF (n=18) and treated with vehicle (n=15). Treatment with LGF was carried out as follows: LGF (5.0 µg/rat) was injected intraperitoneally 6 times at intervals of 3 days (days 0, 3, 6, 9, 12 and 15), maintained for an additional four weeks (the controls were injected with saline during this same time). At the time indicated, the animals were sacrificed and were fixed by intracardiac perfusion with paraformaldehyde at 4% in PBS. The brains were frozen and 20-30 µm sections were prepared in the cryostat. The sections were incubated with antibodies specific for tyrosine hydroxylase (TH, Chemicon International, Temecula, Calif.), neurons (b-tubulin III, Bab Co, Richmond, Calif., and doublecortin, Chemicon International Inc.), glia (GFAP, DakoCytomation Inc., and O1, Sigma Chemical Co, St Louis, Mo.) and neural precursors (nestin, Development Studies Hybridoma Bank, University of Iowa, Ames, Iowa).

The results represent the mean value±SEM of 4 to 10 independent animals. Immunohistochemical analysis was performed using an epifluorescence microscope coupled to the CAST-GRID stereologic analysis software. In each animal, the fluorescence included in the area of the striatum of histologic sections previously selected by defined anteroposterior coordinates was evaluated. Statistical analysis was performed by one-way ANOVA followed by an unpaired t-test or the Bonferroni test for multiple comparisons, and the differences were considered significant for $p \leq 0.05$.

1.1.—Effects of LGF on Dopaminergic Innervation

To determine the degree of degeneration of the nigrostriatal dopaminergic terminals caused by lesion with 6-OHDA, a group of animals (n=4) was sacrificed at 8 weeks post-lesion. Immunohistochemical analysis of coronal sections from 7 different levels of the striatum showed that approximately 30-40% of the surface of the striatum ipsilateral to the lesion is innervated with fibres that are immunopositive for the limiting enzyme in the synthesis of catecholamines, TH. Similar results were obtained in the group of animals sacrificed at 10 weeks post-lesion, which received 6 intraperitoneal (i.p.) injections of vehicle. The intraperitoneal administration of LGF significantly increased TH-positive innervation at almost all the levels of the striatum analysed, this effect being more marked in the more anterior levels (FIG. 1A).

Parkinson's disease is characterized by loss of the dopaminergic neurons of the *substantia nigra* (SN) that project into the striatum. Preservation of the neuronal damage exerted by 6-OHDA on these neurons might contribute to the increase in innervation observed in the animals treated with LGF. However, the loss of TH-positive neurons in the SN of the animals treated with LGF was similar to that observed in the animals treated with vehicle (FIG. 1B).

As already mentioned, LGF promotes neurogenesis in hemiparkinsonian rats (Gonzalo-Gobernado et al., 2007). To determine whether the generation of new dopaminergic neurons could contribute to the increase in the TH-positive innervation observed in the animals treated intraperitoneally with LGF, a group of hemiparkinsonian rats received a daily intraperitoneal injection of 50 mg/kg of bromodeoxyuridine (BrdU) for three weeks, starting the treatment 24 hours after the first injection of vehicle or LGF. Intrastriatal lesion with 6-OHDA increased the incorporation of BrdU in the denervated striatum of these animals by 300%. Immunohistochemical analysis of coronal sections from 1 level of the striatum (AP: −1.8) from the animals treated with vehicle showed similar results (FIG. 1C). However, intraperitoneal administration of LGF did not affect proliferation, since the BrdU-positive cell count was similar in the healthy striatum and the denervated striatum of these animals (FIG. 1C). Independently of the changes in proliferation described, comarkings in the striatal parenchyma of the BrdU-positive cells with neuronal markers (β tubulin III or doublecortin) and/or TH were not observed in any of the experimental groups investigated. Conversely, and although it was recently demonstrated that neurogenesis is stimulated in the SN of healthy rats and rats with lesion with 6-OHDA (Zhao et al., 2003), BrdU-/TH-positive cells were not observed in the SN of the animals treated with LGF.

It can be concluded from all these results that intraperitoneal administration of LGF, just like intrastriatal administration of the factor, promotes the reappearance of the TH-positive terminals in the striatum of rats with intrastriatal lesion with 6-OHDA.

1.2.—Effects of Intraperitoneal Administration of LGF on Rotational Behaviour

The previous works of the group of inventors indicate that LGF administered in the denervated striatum of hemiparkinsonian rats promotes a moderate improvement in the rotational behaviour induced by apomorphine (Bazán et al., 2005, Reimers et al., 2006). To determine whether intraperitoneal administration of LGF is also able to restore motor function, the rotations induced by apomorphine weekly before, during, and two weeks after the period of treatment with the factor, were evaluated in the rats with unilateral lesion of the striatum with 6-OHDA.

As was demonstrated in FIG. 1D, the animals treated with vehicle did not show significant changes in rotational behaviour induced by apomorphine during the period of study. However, 4 weeks after the start of treatment with LGF, a significant decrease in the number of contralateral turns induced by apomorphine in this experimental group was observed, and this effect was maintained during the four weeks subsequent to completion of the treatment with the factor.

We can therefore conclude that intraperitoneal administration of LGF stimulates the regeneration of the dopaminergic terminals damaged in the striatum of hemiparkinsonian rats. Since this route of administration of LGF also promotes a significant behavioural improvement, we propose LGF as a novel factor for use in the treatment of Parkinson's disease.

Example 2

Stimulation of the Serotonin Pathway in the Brain by Injection of LGF by the Intraperitoneal Route The experiments conducted for demonstrating the stimulating activity of LGF, injected by the intraperitoneal route (i.p.) in normal rats, on the serotonin pathway in the brain, are described below.

The possible effect of LGF on the serotoninergic activity in the rat striatum, hypothalamus and hippocampus was investigated. The animals were treated with LGF (5 µg/ratXday, intraperitoneal) on the two days prior to sacrifice. The group of control animals were injected with saline solution in a volume identical to that of the experimental animals.

The serotoninergic activity was evaluated from the accumulation of 5-HTP (5-hydroxytryptophan) after inhibiting decarboxylase with the compound NSD-1015 (Sigma Co.). This compound was administered (125 mg/kg, i.p.) to the two groups of animals that were sacrificed one hour after administration of LGF or saline. The animals were decapitated and the brain was quickly extracted on ice, followed by dissection of the right striatum and right hippocampus. The rest of the brain was kept frozen for later dissection of the hypothalamus. The tissue samples were homogenized by sonication in $ClO_4H$ 0.4 N with 0.002% of ascorbic acid, they were centrifuged and the supernatant was used for determining the 5-HTP content by reversed-phase high-performance liquid chromatography (HPLC) and electrochemical detection. The methods are described in detail in Marco et al., 1979, Marco et al., 1999. The precipitate was redissolved in 0.5 N NaOH for protein determination and the final concentration of 5-HTP was obtained in relation to the latter. The results were expressed as mean value±SEM.

The results, which are shown in Table 1, indicate a significant increase in 5-HTP accumulation both in the striatum and in the hippocampus or in the hypothalamus after the animals were treated with LGF, which is interpreted, functionally, as an increase in serotoninergic activity in these areas of the brain.

TABLE 1

Levels of 5-http in the brain of animals treated with LGF

| TISSUE | TREATMENT | 5-HTP (pmol/mg prot.) | n (number of samples) |
|---|---|---|---|
| Striatum | Control | 10.88 ± 0.71 | 12 |
|  | LGF | 13.20 ± 0.75* | 12 |
| Hippocampus | Control | 8.03 ± 0.35 | 12 |
|  | LGF | 10.30 ± 0.60** | 12 |

TABLE 1-continued

Levels of 5-http in the brain of animals treated with LGF

| TISSUE | TREATMENT | 5-HTP (pmol/mg prot.) | n (number of samples) |
|---|---|---|---|
| Hypothalamus | Control | 26.55 ± 0.99 | 12 |
| | LGF | 30.13 ± 1.35* | 12 |

*$p < 0.05$ compared with the control
**$p > 0.005$ compared with the control

In view of the activity of LGF on Parkinson's disease, injected by the intraperitoneal route, as well as the activity on the serotonin pathway, which might imply its action in several very different situations, it is to be hoped that LGF has regenerative and reparative activity in other neurodegenerative diseases, such as Huntington's disease, amyotrophic lateral sclerosis, ataxias etc.

BIBLIOGRAPHIC REFERENCES

Abakumova y cols., *J. Hepatology*, 21:947-952, 1994
Azmitia E C y cols., *Int Review Neurobiol*, 77:51-56, 2007.
Bagdy G y cols, *J Neurochem*, 100:857-73, 2007.
Bazán E, y cols., *Mapfre Medicina*, 16: 237-247, 2005.
Bilgen M, y cols., *Magnetic Res in Med*, 45:614-22, 2001.
Bilgen M, y cols., *Magnetic Res in Med*, 20:337-41, 2002.
Buhot M C y cols., *Ann Med*, 32:210-21, 2000.
Díaz Gil y cols., *Biochem J*, 234:49-54, 1986.
Díaz Gil y cols., *Biochem J.*, 243:443-448, 1987.
Díaz Gil y cols., *Hepatology*, 8:484-486, 1988.
Díaz Gil y cols., *Mol. Biol & Medicine*, 6:197-207, 1989.
Díaz Gil y cols., *Growth Regulation*, 4:113-122, 1994a.
Díaz Gil y cols., *NATO ASI Series "Cell Biology"*, vol. 88:275-288, 1994b.
Díaz Gil y cols., *J Hepatology*, 6:1065-1072, 1999.
Díaz Gil y cols., *J Hepatology*, 38:598-604, 2003.
Ding W X y cols., *J Cell Mol Med*, 8(4):445-54, 2004.
Fallon J, y cols., *Proc Nat Acad Scienc USA*, 97:14686-91, 2000.
Gao J y cols., *Brain Res*, 945:60-70, 2002.
Ghinea y cols., *J. Cell Biol.*, 107:231-239, 1988
Gonzalo-Gobernado R, y cols., *Revista de Neurologia*, 45:187, 2007.
Gordh T, y cols., *Pain*, 124:211-21, 2006.
Grahame-Smith D S y cols, *Int Clin Psychopharmacol*, 6 (suppl 4):5-13; 1992.
Horner P J, *Exp Neurol*, 142:226-43, 1996.
Jaeger C B, y cols., *Exp Neurol*, 144(2):381-99, 1997.
Kaye W H y cols, *Physiology & Behaqviour*, 82:73-81, 2005.
Kettelhut I y cols., *Proc. Natl. Acad. Sci. USA*, 84:4273-7, 1987.
Kirik D, y cols., *Exper Neurol* 152: 259-277, 1998.
Lloyd H, y cols. *Sce*, 170:1212-13, 1970.
Maikos J T, *J Neurotrauma*, 24:492-507, 2007.
Malhi H y cols., *Hepatology*, 43:S31-S44, 2006.
Marco E J y cols., *Nauny-Scmiedeberg's Arch Pharmacol*, 306:75-9, 1979.
Marco E J y cols, *Stroke*, 30:1695-1701, 1999.
Meltzer C C y cols, *Neuropsychopharmacology*, 18:407-430, 1998.
Morioanu y cols., *Eur. J. Cell Biol.*, 53:20-26, 1990.
Pardridge W P, *Am Soc Exp Neuro Ther*, 2:3-14, 2005.
Pardridge W P, *Pharmaceutical Res*, 24:1733-44, 2007.
Pettersson C A, y cols., *Acta Neurol Scand*, 82:21-7, 1990.
Popovich P G, y cols., *Exp Neurol*, 142:258-75, 1996.
Reese T S, y cols., *J Cell Biol*, 4:200-17, 1967.
Reimers, D, y cols., *J Histochem Cytochem*, 54:457-65, 2006.
Reinhardt R R and Bondy C A, *Endocrinology*, 135:1753-61, 1994.
Sharma H S, "The blood-spinal cord and brain barriers in health and disease", Academic Press, Elsevier, págs. 437-518, 2004.
Schnitzer y cols., *J. Biol. Chem.*, 267:24544-53, 1992.
Smythies J y cols, *Int Review Neurobiol*, 64:217-68, 2005.
Somoza y cols., *Cardiovascular Research*, 69(3):764-71, 2006.
Sun Y, y cols., *J Clin Invest*, 111:1843-51, 2003.
Torp R y cols, *Tidsskr Nor Laegeforen*, 126:899-901, 2006.
Trauner M y cols., *J Gastroentrol Hepatol*, 14:946-59, 1999
Whetstone W D, y cols., *J Neurosci Res*, 74:227-39, 2003.
Wood J D, y cols., *J Neurosurg*, 90(1 Suppl):115-20, 1999.
Yan Q S y cols, *Acta Neuropathol (Berl)*, 101:256-70, 2001.
Zhao M, y cols, *Proc Natl Acad Sci USA*, 100:7925-7930, 2003.

The invention claimed is:

1. A method of treating Parkinson's disease, said method comprising systemically administering an effective amount of liver growth factor to a human being or an animal in need thereof.

2. The method according to claim 1, wherein the administering is by an intraperitoneal route.

3. The method according to claim 1, wherein the administering is by an intravenous route.

4. The method according to claim 1, wherein the human or animal has an intact blood-brain barrier.

5. The method according to claim 1, wherein the liver growth factor is human liver growth factor.

* * * * *